United States Patent [19]
McLean et al.

[11] Patent Number: 6,023,923
[45] Date of Patent: Feb. 15, 2000

[54] DRIVE SHAFT SUPPORT FOR MOWER CONDITIONERS

[75] Inventors: Kenneth W. McLean; Steven J. Campbell, both of New Holland, Pa.

[73] Assignee: New Holland North America, Inc., New Holland, Pa.

[21] Appl. No.: 09/245,730

[22] Filed: Feb. 8, 1999

Related U.S. Application Data

[63] Continuation of application No. 08/752,123, Nov. 20, 1996, abandoned
[60] Provisional application No. 60/007,507, Nov. 22, 1995, and provisional application No. 60/009,237, Dec. 26, 1995.

[51] Int. Cl.$^7$ ................................................. A01D 34/00
[52] U.S. Cl. ............................................. 56/218; 56/14.9
[58] Field of Search ................................. 56/10.3, 11.4, 56/11.5, 11.3, 11.7, 13.5, 14.1, 14.5, 16.4, 218, 11.9, 15.2, 15.4; 74/15.2, 15.6, 15.66, 15.69; 180/53.1, 53.3; 403/260

[56] References Cited

U.S. PATENT DOCUMENTS

| | | |
|---|---|---|
| 3,413,926 | 12/1968 | Ayson ................................. 403/260 X |
| 3,434,366 | 3/1969 | Raso et al. ........................... 403/260 X |
| 4,815,262 | 3/1989 | Koch ...................................... 56/13.6 |
| 4,840,019 | 6/1989 | Pingry ..................................... 56/13.6 |
| 4,947,629 | 8/1990 | Ermacora ................................ 56/13.6 |
| 4,955,187 | 9/1990 | Van der Lely .......................... 56/13.6 |
| 5,018,345 | 5/1991 | Walters .................................... 56/14.9 |
| 5,056,302 | 10/1991 | Rosenbalm et al. .................... 56/10.3 |
| 5,099,937 | 3/1992 | McLean ................................. 180/53.3 |

*Primary Examiner*—Robert Pezzuto
*Attorney, Agent, or Firm*—Larry W. Miller; John W. Stader; Frank A. Seemar

[57] ABSTRACT

A curved implement tongue improves the turning characteristics of the implement, such as a mower-conditioner. The tongue is bent in the horizontal plane and incorporates a generally vertical box section at the end of the tongue. The tongue supports a driveline transmitting rotational power from a prime mover to the operative components of the mower-conditioner. The driveline incorporates a clutch assembly mounted on the input shaft of a bevel gearbox. The forward end of the input shaft is formed with a conical surface that mates with a corresponding conical hub bore formed within the clutch assembly. The end of the input shaft is formed as a truncated cone to provide a gap between the end of the shaft and the bottom of the bore and assure a proper seating of the two members.

3 Claims, 4 Drawing Sheets

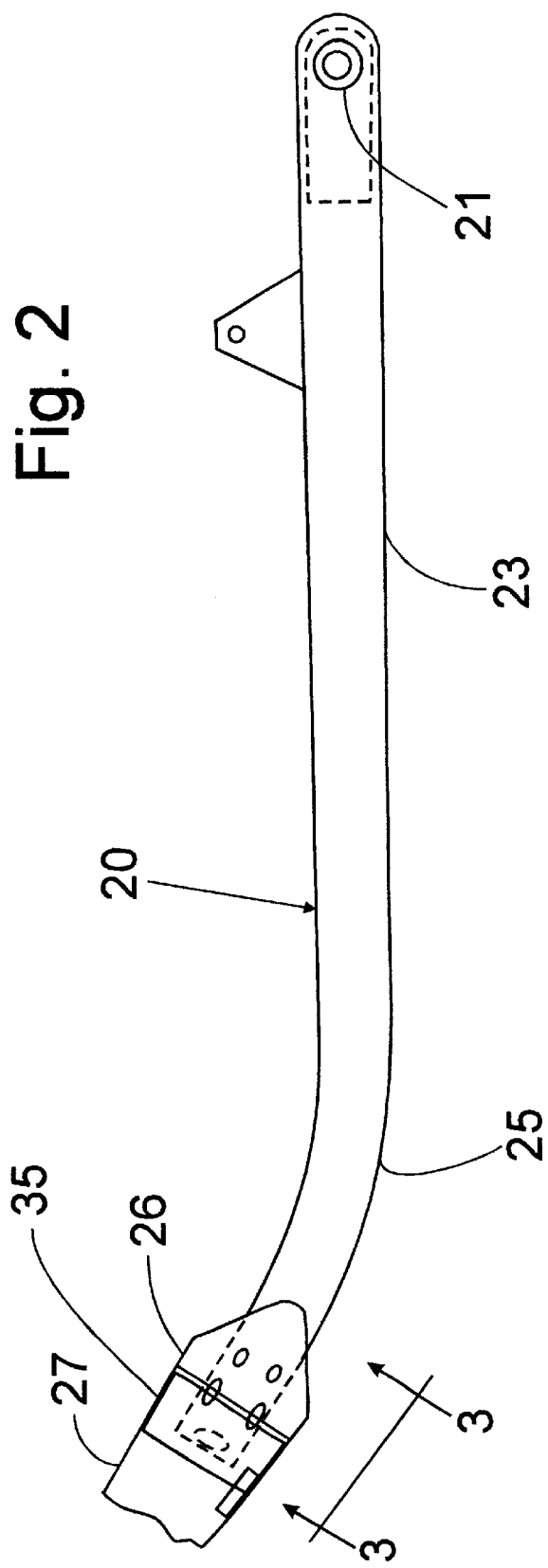
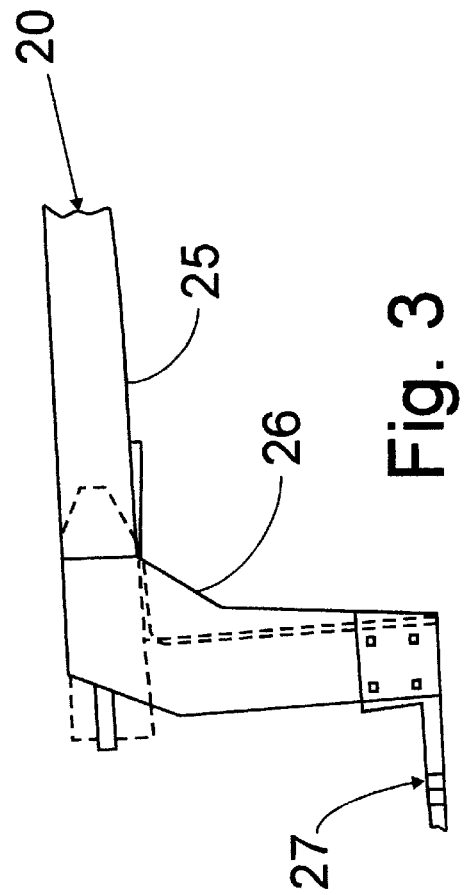

DRIVE SHAFT SUPPORT FOR MOWER CONDITIONERS

CROSS-REFERENCE TO RELATED APPLICATIONS

This application is a continuation of U.S. patent application Ser. No. 08/752,123, filed Nov. 20, 1996, now abandoned, claiming domestic priority on U.S. Provisional Patent Application Ser. No. 60/007,507, filed Nov. 22, 1995, and U.S. Provisional Patent Application Ser. No. 60/009,237, filed Dec. 26, 1995.

BACKGROUND OF THE INVENTION

Pull-type harvesting implements utilize a draft tongue to connect the implement to the hitch of a tractor. The tongue is pivotally supported from the frame of the implement to permit the tongue to pivotally move relative thereto so that the implement can move from a transport position directly behind the tractor to an operative position behind the tractor, but offset to the side thereof.

The draft tongue also supports a drive line connectable to the power-takeoff shaft of the tractor to deliver rotational power to the operative components of the harvesting implement, such as the cutting mechanism and other crop harvesting apparatus supported from the frame of the implement. The drive line typically incorporates several universal joints to permit bends in the drive line to accommodate the pivotal movement of the tongue as the implement is moved between the transport and operative positions.

Typically, the frame of the harvesting implement will be made mobile through a pair of transverse wheels. When the harvesting implement is operated in the operative position and offset outboard of the tractor, it will often be necessary to change the direction of travel of the implement, which is accomplished through the turning of the tractor. If an imaginary line is extended from the rear axle of the tractor to a line corresponding to the axle of the implement interconnecting the transverse wheels, a point of intersection is obtained. The closer the point of intersection is to one of the implement wheels, the tighter the implement will be turned.

Several tongue and hitch designs have been provided to provide tighter turning characteristics. One such design is commonly referred to as the equal angle hitch mechanism in which the pivot point between the draft tongue and the tractor is located midway between the first two universal joints of the drive line so that any turns result in equal turning or deflection angles in the first two universal joints.

Another design is commonly referred to as the swivel hitch design as represented in U.S. Pat. No. 5,099,937. In this design, the turning movement is pivoted through a gearbox to eliminate the angular deflections in the drive line universal joints. While this swivel hitch design allowed a greater turning movement of the tractor relative to the draft tongue, and as a result moved the point of intersection of the line of the tractor axle with the line of the implement axle closer to the left implement wheel, further improvement is still available.

John Deere Company developed a bent implement tongue design to improve the turning characteristics of the implement, as is represented in U.S. Pat. No. 5,018,345. While this draft tongue design improves the implement turns, the tongue requires a bumper on the side of the tongue to prevent damage due to interference with the tractor tire.

It would be desirable to provide an implement tongue design that would be aesthetically pleasing, while improving implement turning characteristics.

Disc cutterbars have been utilized in agricultural harvesting implements for many years. Each disc cutterbar includes a plurality of transversely spaced disc cutters driven for rotation about a generally vertical axis. Each disc cutter has two or three knives pivotally mounted on the periphery thereof to sever standing crop from the ground through an impact action. For background information on the structure and operation of disc cutterbars, reference is made to U.S. Pat. No. 4,815,262, issued to E. E. Koch and F. F. Voler, the descriptive portions thereof being incorporated herein by reference.

The construction of disc cutterbars has evolved over the years to the configuration of having a modular construction with cutter modules and spacer modules, such as shown in U.S. Pat. No. 4,840,019, issued to L. J. Pingry, the descriptive portions of which are incorporated herein by reference. In some instances, the cutter modules and the spacer modules were integrally formed into one unit such as shown and described in U.S. Pat. No. 4,947,629, issued to R. Ermacora and H. Neuerburg.

It has been found that the specific use of the disc cutterbar apparatus, e.g. whether used as part of a disc mower, such as shown and depicted in U.S. Pat. No. 4,955,187, issued to C. van der Lely, which is typically supported at one end, or as part of a disc mower-conditioner which usually provides support to the cutterbar at both opposing ends thereof, carries with that use a different set of design parameters than other machines in which the cutterbar is utilized.

On a disc mower-conditioner drive shaft, the secondary power-takeoff drive shaft is typically supported in a cantilevered manner off of the front of the splined input shaft of the main bevel gearbox. Included on the secondary drive shaft is a constant velocity universal joint assembly and a slip clutch, both of which are quite heavy. The power-takeoff shaft is retained on the input shaft by a split clamp hub design.

As the power-takeoff shaft turns at high speeds, the centrifugal forces resulting from the unbalanced shaft/universal joint/clutch assembly are carried by the input shaft spline teeth and clamp joint. The secondary couple from the universal joints in the constant velocity joint are also imposed on the input shaft. The spline fit with the clutch hub is loose intentionally so that the assembly can be installed over the splined shaft.

This looseness of the external and internal spline teeth permits the assembly to be positioned off-center to the shaft. The centrifugal forces from the off-center mass and the forces of the secondary couple cause the assembly to whirl about the shaft centerline. The motion of the inner and outer splined parts wears the spline teeth causing more spline tooth clearance and increased relative motion, eccentricity and force as the machine is used.

The clamped split hub retains the splined hub to the splined shaft adjacent to the clamp, but not away from the clamp area. The reaction from the secondary couple is carried partly by the clamped hub portion which causes relative motion between the clamped mating surfaces in the clamp area. The spline teeth in the clamp area are, therefore, subjected to the same wear problem.

The centrifugal forces from the eccentric constant velocity universal joint/clutch assembly and from the secondary universal joint couple are supported by the bevel gearbox input shaft. The alternating forces can cause the input shaft to fail in fatigue resulting in the shaft to have to be made larger and/or be heat treated to withstand the forces. The support of the bevel gearbox also carries the vibrating forces and is, therefore, prone to failure as well.

Several alternative design solutions have been proposed to resolve the fixation problem of the clutch hub on the shaft, including an axially placed bolt that screws into the end of the input shaft to clamp the clutch hub against the end of the input shaft and rigidly fix the clutch for better support thereof, but did not adequately resolve the problem as these designs became loose over time. A further disadvantage was recognized in that the alternative designs did not include an alignment feature to position the drive shaft/constant velocity joint/clutch assembly concentrically about the shaft centerline.

SUMMARY OF THE INVENTION

It is an object of this invention to overcome the disadvantages of the prior art by providing a curved implement tongue for a mower-conditioner.

It is a feature of this invention that the implement tongue extending forwardly of the frame of the mower-conditioner for attachment to a prime mover, such as a tractor, is bent in a horizontal plane at the forward end of the tongue.

It is an advantage of this invention that the curved implement tongue improves turning characteristics for the mower-conditioner.

It is another feature of this invention that the driveline supported by the curved implement tongue incorporates a pair of constant velocity joints to accommodate any misalignment of the driveline during sharp turns of the implement.

It is another advantage of this invention that the implement tongue does not require an interference structure that is engageable with the tractor tire to restrict the severity of the implement turn to prevent unacceptable joint angles in the implement driveline.

It is still another advantage of this invention that the joint angles in the driveline are not excessive whenever the implement is turned so sharply that the tractor tire can rub against the tongue structure.

It is still another feature of this invention that the forward end of the tongue incorporates a generally vertical box section to support a gearbox operable to elevate the driveline.

It is another object of this invention to provide a curved implement tongue for a mower-conditioner which is durable in construction, inexpensive of manufacture, carefree of maintenance, facile in assemblage, and simple and effective in use.

It is still another object of this invention to overcome the disadvantages of the prior art by providing a conical shaft support for the driveline of a mower-conditioner.

It is yet another feature of this invention that the clutch assembly incorporates a conical hub bore to receive the mating conical distal end of the input shaft for improved support thereof.

It is yet another advantage of this invention that the contact between the conical shaft end and the conical hub bore centers the assembly to minimize any eccentricity of the rotating mass.

It is a further feature of this invention that the input shaft end is formed as a truncated cone to provide a gap between the end of the shaft and the bottom of the hub bore to assure proper seating of the shaft into the bore.

It is a further advantage of this invention that the elimination of the relative motion between the clutch hub and the end of the shaft lessens the chance of failure of the driveline components due to eccentric forces incurred therein.

It is yet another object of this invention to provide a shaft support within a clutch assembly for a mower-conditioner which is durable in construction, inexpensive of manufacture, carefree of maintenance, facile in assemblage, and simple and effective in use.

These and other objects, features and advantages are accomplished according to the instant invention by providing a curved implement tongue to improve the turning characteristics of the implement. The tongue is bent in the horizontal plane and incorporates a generally vertical box section at the end of the tongue. The tongue supports a driveline transmitting rotational power from a prime mover to the operative components of the mower-conditioner. The driveline incorporates a clutch assembly mounted on the input shaft of a bevel gearbox. The forward end of the input shaft is formed with a conical surface that mates with a corresponding conical hub bore formed within the clutch assembly. The end of the input shaft is formed as a truncated cone to provide a gap between the end of the shaft and the bottom of the bore and assure a proper seating of the two members.

BRIEF DESCRIPTION OF THE DRAWINGS

The advantages of this invention will be apparent upon consideration of the following detailed disclosure of the invention, especially when taken in conjunction with the accompanying drawings wherein:

FIG. 2 is a bottom plan view of the draft tongue;

FIG. 3 is a partial elevational view of the forward portion of the draft tongue corresponding to lines 3—3 of FIG. 2;

DETAILED DESCRIPTION OF THE PREFERRED EMBODIMENT

Figure 1:
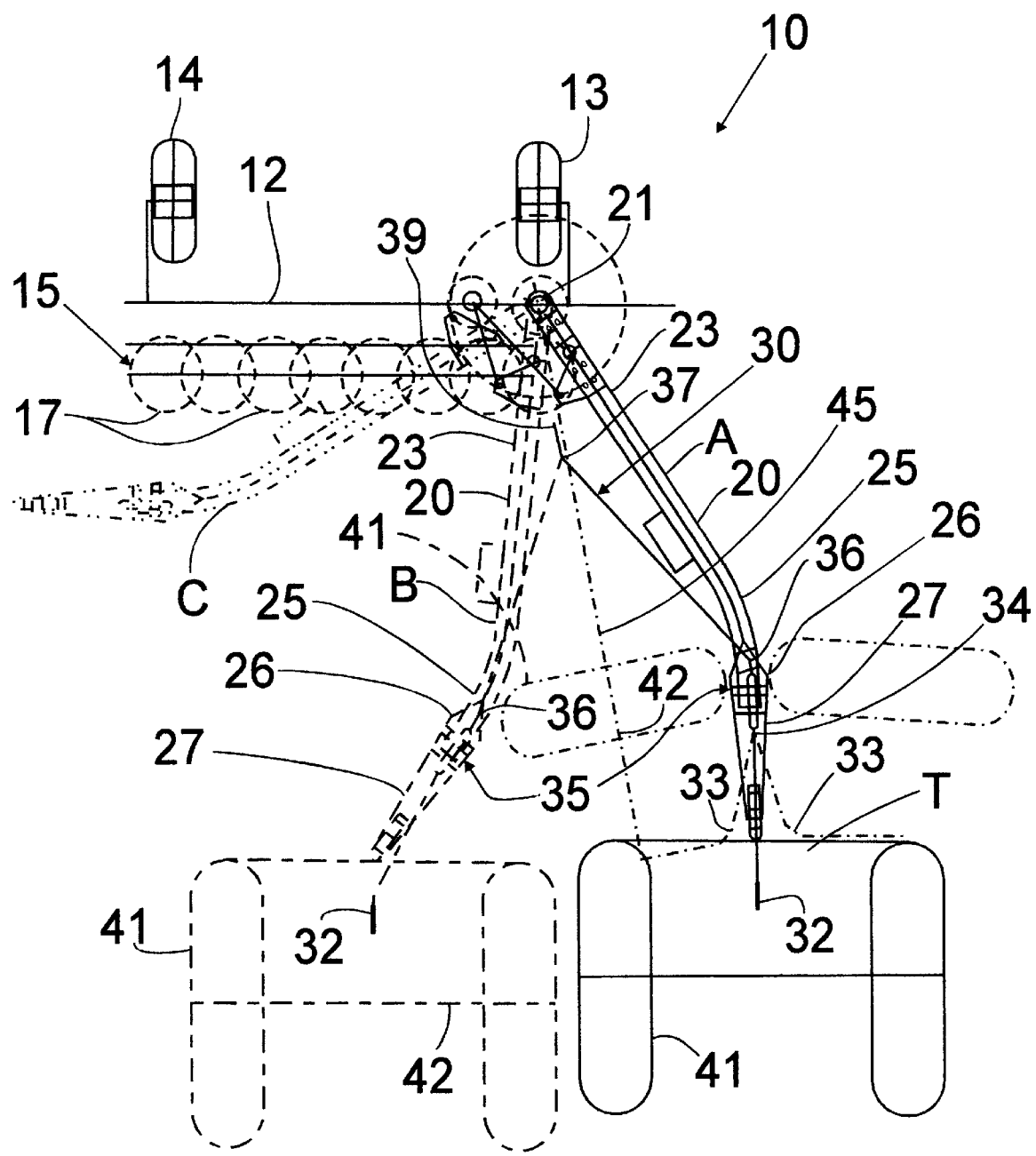
FIG. 1 is a schematic top plan view of a draft tongue for a harvesting implement commonly referred to as a disc mower-conditioner, the tongue being pivotally hitched to a tractor and being shown in three pivoted positions, operative, transport and shipping, the tractor tires being shown in the operative and transport positions and while turning left and right in the operative position.
Figure 4:
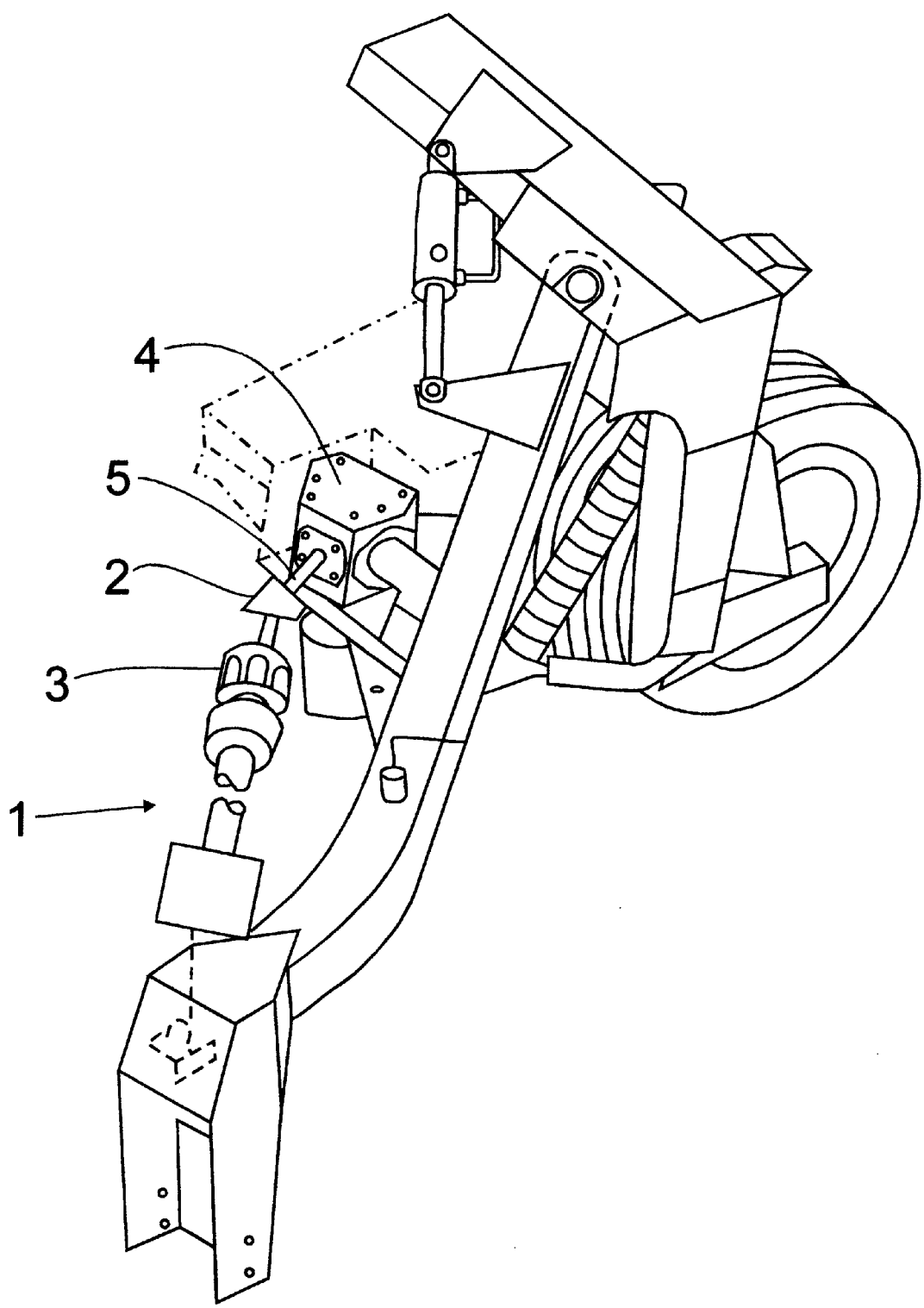
FIG. 4 is a partial exploded perspective view of a disc mower-conditioner trail frame assembly depicting the left end of the header assembly suspended therefrom.
Figure 5:
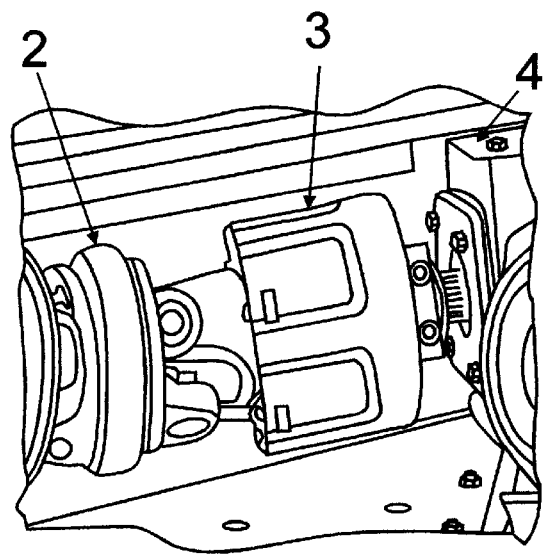
FIG. 5 is an enlarged elevational view of the constant velocity universal joint/slip clutch assembly.

The structure of the disc mower-conditioner can best be found in Applicant's co-pending U.S. patent application Ser. No. 08/670,060, entitled "Disc Mower-Conditioner", the descriptive portions of which are incorporated herein by reference. Furthermore, the structure of the modular disc cutterbar forming an integral part of the header assembly of the disc mower-conditioner is best described in Applicant's co-pending U.S. patent application Ser. No. 08/673,604, entitled "Disc Cutterbar for Agricultural Implements", the descriptive portions of which are incorporated herein by reference.

Referring to all of the drawings, it can be seen that the implement 10, shown in the form of a disc mower-conditioner, is provided with a frame 12 made mobile through support of a left ground engaging wheel 13 and a right ground engaging wheel 14. A transverse disc cutterbar 15 is forwardly supported from the frame 12 and comprises a plurality of transversely spaced rotatable disc members 17 that sever standing crop through an impact action.

The frame 12 is pivotally connected via a pivot joint 21 at the left side thereof to a draft tongue 20 that extends forwardly therefrom to connection with the tractor T. The tongue 20 is formed preferably from a tubular beam of a cross sectional configuration sufficient to withstand the draft forces, such as a six inch square tubular beam. The rearward portion 23 of the tongue 20 extends linearly from the pivot 21 to a curved portion 25 near the distal hitch end 27 of the tongue 20. Since the implement 10 is customarily operated to the right of the tractor T, the curved portion 25 of the tongue 20 displaces the distal hitch end 27 horizontally to the right of a line extending forwardly from the rearward linear portion 23.

The forward or distal hitch end 27 is constructed of a generally vertically oriented box section 26 to support a fixed gear box 35 that elevates the drive line 30 from the elevation of the tractor power-takeoff shaft 32 to the elevation desired to extend the drive line 30 rearwardly to the implement while being supported from the tongue 20. The drive line 30 preferably incorporates a first constant velocity joint 33 to accommodate any misalignment between the tractor power-takeoff shaft 32 and the drive line 30. Preferably, the first constant velocity joint 33 is operable through a displacement angle of 80 degrees as operation may be desirable while the tractor is undertaking either a left or right turn, as demonstrated in FIG. 1, with the tongue in the operative position A.

The drive line 30 preferably further incorporates a second contact velocity joint 34 forwardly of the gear box 35 to accommodate bends in the drive line 30 during left and right turns. A third constant velocity joint 36 is positioned in the drive line 30 immediately rearwardly of the gear box 35 to accommodate angular displacement of up to 50 degrees of the drive line 30 when the tongue is moved between the operative position A and the transport position B. The shipping position C of the tongue 20 is used only for shipping the implement by carrier. A fourth constant velocity joint 37 is positioned forwardly of the fixed support 39 of the drive line 30 from the frame 12 to accommodate also the movement of the tongue 20 between the operative position A and the transport position B.

As can be seen in FIG. 1, the right hand turn of the tractor T places the adjacent rear tire 41 of the tractor T at the curved portion 25 of the tongue 20, which permits a greater turning angle for the tractor T than if the tongue 20 were to extend linearly from the pivot 21 to the distal hitch end 27. As a result, an imaginary line 45 corresponding to an extension of the rear tractor axle 42 intersects the implement axle very close to the left implement wheel 13. The result is that the hard right turns of the tractor T will substantially result in the implement 10 being turned about the left wheel 13, thereby creating sharp implement turns needed to make efficiently square corners at the end of a field of crop being harvested.

The resolution of the fixation problem outlined above with respect to the eccentric and centrifugal driveline forces causing excessive wear in the splined connection of the driveline is provided by shaping the end of the input shaft 5 with a conical end 9 that seats into a corresponding conical shaped hole in the end of the clutch hub bore 6A. A gap 9A is provided between the end of the shaft 5 and the hub bore 6A to ensure that the conical surfaces seat fully. The angle of the shaft end 9 and the hub bore 6A is nominally identical so that they seat against each other when a screw SA is utilized to push the hub 4 onto the shaft 5.

Figure 6:
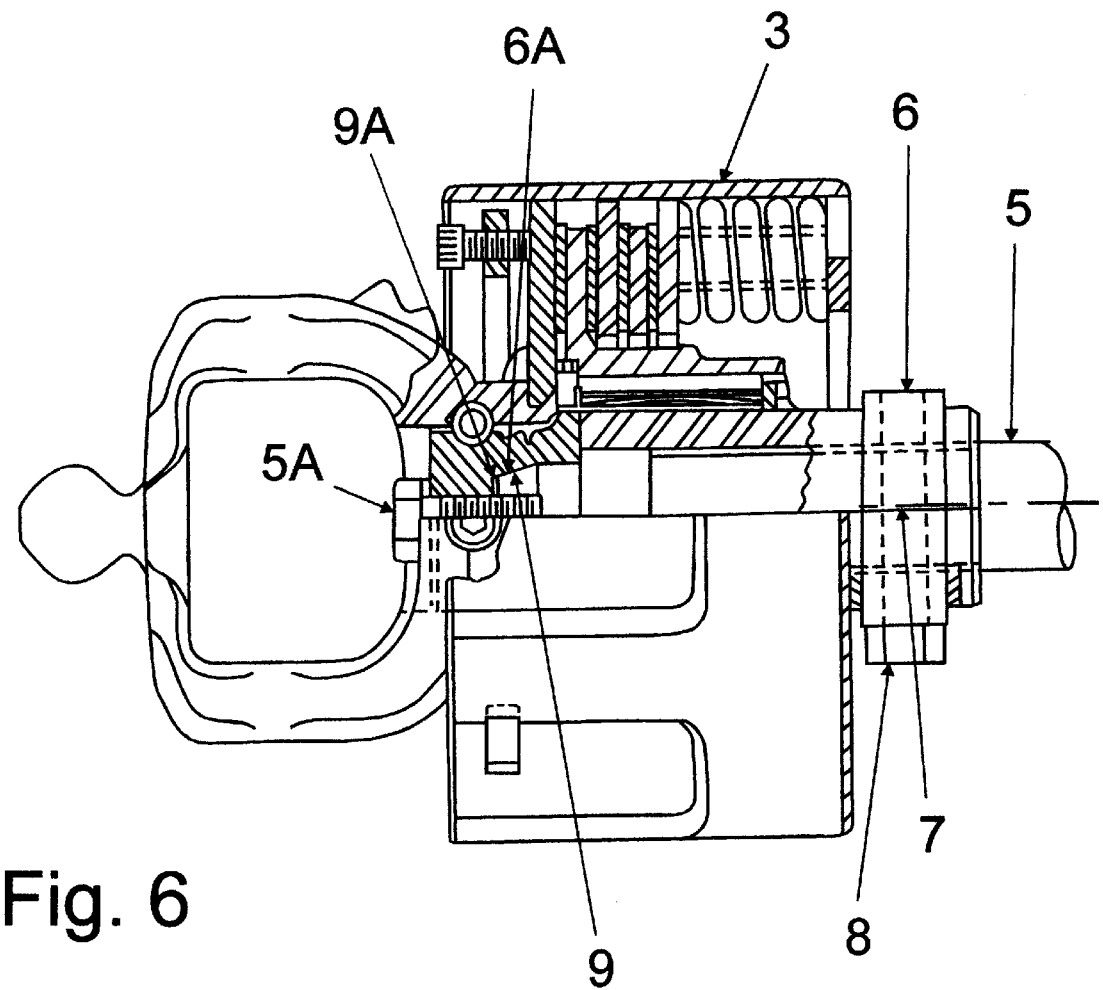
FIG. 6 is an enlarged partial cross-sectional view of the slip clutch and input shaft depicted in FIG. 5.

The power-takeoff shaft assembly 1 having a constant velocity universal joint 2 and a slip clutch 3 are supported by the input shaft 5 of a bevel gearbox 4. The clutch hub 6 is split and is clamped onto the shaft 5 with a bolt 8 adjacent the bevel gearbox 4. The forward end 9 of the input shaft 5 is machined to form a conical shape, as best seen in FIG. 6. The bottom of the clutch hub bore 6A is also machined to form a conical shape corresponding to the end 9 of the input shaft 5, such that when the hub 6 is pushed onto the shaft 5 by the clamp bolt 5A, the two conical surfaces come in contact to form a secondary support of the clutch assembly. A gap 9A is located between the shaft end 9 and the clutch hub bore 6A to ensure that the conical surfaces of the end 9 and the bottom of the hub bore 6A will seat fully.

The contact of the angled surface of the two parts 9 and 6A supports the constant velocity universal joint and the clutch assembly centrifugal forces as well as the universal joint secondary couple forces. In addition, the conical surfaces center the universal joint/clutch assembly on the shaft centerline to reduce the eccentricity of the driveline design and, therefore, reduce the centrifugal forces generated by an off-center rotating mass.

The contact between the input shaft and the hub bore conical surfaces of this driveline design centers the assembly of the power-takeoff shaft/constant velocity joint/clutch to provide the advantage of minimizing the eccentricity of the rotating mass relative to the shaft and, as a result, minimizing the centrifugal forces imposed on the shaft. This driveline design also has the advantage of eliminating the relative movement between the shaft external and internal spline teeth, which prevents wear therebetween and the resultant increased looseness. Furthermore, the more precisely positioned universal joint/clutch assembly and the elimination of the relative motion between the clutch hub and the input shaft greatly reduces the alternating forces on the input shaft and bevel gearbox support, thereby lessening the chance that these components will fail due to fatigue.

A variation to this driveline design would be to use a close tolerance cylindrical portion of the shaft at its distal end, instead of the aforementioned machined conical shape, which cylindrical shape would slide into a close tolerance bore inside the hub, with the axially positioned bolt securing the hub to the shaft. The movement of the hub relative to the shaft would be limited to the clearance between the shaft and the bore. It would be anticipated, however, that the axially positioned bolt may be difficult to keep tight due to the motion between the shaft and the hub bore. Accordingly, the driveline design described above and incorporating the machined conical surfaces to center the assembly on the shaft is preferred.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention. Accordingly, the following claims are intended to protect the invention broadly as well as in the specific form shown.

Having thus described the invention, what is claimed is:

1. In a driveline for a mower-conditioner having a frame adapted for movement over the ground, said frame having draft means for connection to a prime mover for supplying operative power thereto; a header movably supported from said frame and including a cutterbar operable to sever standing crop material from the ground, said driveline operably connecting said prime mover and said header to deliver rotational power to said cutterbar to power the operation thereof, an improvement to said driveline comprising:

a cylindrical input shaft having a distal end formed with a conical surface;

a clutch assembly supported on said input shaft and being formed with a central hub bore having an upper portion formed in a cylindrical configuration to mate with said cylindrical input shaft and a conical bottom portion mating with said conical surface on the distal end of said input shaft to receive said cylindrical input shaft and said distal end with said conical surface therewithin and to seat said clutch assembly axially with respect to said input shaft.

2. The driveline of claim 1 wherein said input shaft conical surface is formed as a truncated cone to provide a gap between the end of the input shaft and the conical bottom portion of said central hub bore when said input shaft is engaged into said clutch assembly so that the respective conical surfaces seat fully.

3. The driveline of claim 2 wherein said input shaft extends forwardly from a bevel gearbox to support said clutch assembly thereon.

* * * * *